United States Patent
Newman et al.

(10) Patent No.: US 9,006,661 B1
(45) Date of Patent: Apr. 14, 2015

(54) COMPACT THZ FOCAL PLANE IMAGING ARRAY WITH INTEGRATED CONTEXT IMAGING SENSORS AND ANTENNAE MATRIX

(71) Applicant: Exelis, Inc., McLean, VA (US)

(72) Inventors: Jeffrey Daniel Newman, Pittsford, NY (US); Paul Poo-Kam Lee, Pittsford, NY (US); Robert Dean Fiete, Fairport, NY (US)

(73) Assignee: Exelis, Inc., McLean, VA (US)

( * ) Notice: Subject to any disclaimer, the term of this patent is extended or adjusted under 35 U.S.C. 154(b) by 237 days.

(21) Appl. No.: 13/665,114

(22) Filed: Oct. 31, 2012

(51) Int. Cl.
*G01J 5/02* (2006.01)
*G01J 1/42* (2006.01)

(52) U.S. Cl.
CPC .................................... *G01J 1/42* (2013.01)

(58) Field of Classification Search
CPC .................. G01N 31/3581; G01N 21/3586
USPC .................................. 250/349, 341.1–341.8
See application file for complete search history.

(56) References Cited

U.S. PATENT DOCUMENTS

| | | | |
|---|---|---|---|
| 5,550,373 | A | 8/1996 | Cole et al. |
| 5,561,523 | A | 10/1996 | Blomberg et al. |
| 6,621,083 | B2 | 9/2003 | Cole |
| 7,489,024 | B2 | 2/2009 | Socher et al. |
| 2005/0179606 | A1 | 8/2005 | Holly |
| 2006/0152412 | A1 | 7/2006 | Evans et al. |
| 2011/0163932 | A1 | 7/2011 | Mosbacker |
| 2011/0254959 | A1* | 10/2011 | Seppa et al. ................... 348/164 |
| 2011/0315880 | A1 | 12/2011 | Nemirovsky |
| 2012/0032082 | A1* | 2/2012 | Pradere et al. .............. 250/341.1 |
| 2012/0091342 | A1* | 4/2012 | Berger et al. ............... 250/338.4 |
| 2012/0261575 | A1* | 10/2012 | Averitt et al. .................. 250/332 |
| 2012/0261579 | A1 | 10/2012 | Ramaswamy et al. |
| 2013/0082181 | A1* | 4/2013 | Corcos et al. ................. 250/349 |
| 2013/0099118 | A1* | 4/2013 | Tomioka ........................ 250/332 |
| 2013/0256535 | A1* | 10/2013 | Meijer et al. .................. 250/340 |

FOREIGN PATENT DOCUMENTS

| | | |
|---|---|---|
| DE | 10 2008 031 751 | 8/2009 |
| WO | WO 92/04653 | 3/1992 |

OTHER PUBLICATIONS

Perenzoni et al., "A monolithic visible, infrared, and terahertz 2D detector," 2010, $35^{th}$ International Conference on Infrared, Millimeter, and Terahertz Waves, pp. 1-2.*

Entire Patent Prosecution History of U.S. Appl. No. 14/223,454, filed Mar. 24, 2014, Entitled, "Terahertz Tunable Filter With Microfabricated Mirrors".

(Continued)

*Primary Examiner* — Kiho Kim

(74) *Attorney, Agent, or Firm* — RatnerPrestia

(57) ABSTRACT

A monolithic focal plane array (FPA) of an imaging system includes an array of multiple pixel unit cells disposed on a substrate. Each pixel unit cell includes: a first array of THz antennae disposed on a top layer of the substrate, and a second array of context imaging pixels disposed on the top layer of the substrate. The first and second arrays are interleaved on the top layer of the substrate. In addition, each THz antenna in the first array is shaped either in a bow-tie, circular or tuned waveguide configuration, and each context imaging pixel in the second array is shaped in a circular, or rectangular configuration.

17 Claims, 8 Drawing Sheets

(56) References Cited

OTHER PUBLICATIONS

Entire Patent Prosecution History of U.S. Appl. No. 13/785,435, filed May 3, 2013, Entitled, "Compact THz Imaging Detector With an Integrated Microspectrometer Spectral Tuning Matrix".

Machine Translation of DE 10 2008 031 751 (Hohmuth et al.).

P. Krippner, Y. Kühner, J. Mohr, and V. Saile, "Microspectrometer System for the Near Infrared Wavelength Range Based on the LIGA Technology", Proceedings of SPIE vol. 3912, 2000, pp. 3912-3918.

J.N. McMullin, X. Chen, "Integrated Diffraction Grating for Lab-on-a-Chip Microspectrometer", Photonics West 2005, San Jose Convention Center, Jan. 22-27, 2005, p. 5699-76.

G. Chen, Z. Wen, Y. Xu, Z. Jiang, B. Zhang, Miniature Bio-Chemical Analytical System Based on Microspectrometer, Photonics West 2005, San Jose Convention Center, Jan. 22-27, 2005, p. 5719-15.

R.A. Crocombe, D. C. Flanders and W. Atia, "Micro-Optical Instrumentation for Process Spectroscopy", *Proc. of SPIE*, 5591, 2004, pp. 11-25.

Adrian J. Keating, Jarek Antoszewski, Konkaduw K.M.B.D. Silva, Kevin J. Winchester, Thuyen Nguyen, John. M. Dell, Charles A. Musca, Lorenzo Faraone and Olivia Samardzi; *Fabry-Perot MEMS Microspectrometers Spanning the SWIR and MWIR*, Proc. of SPIE vol. 6542, 65423G, 2007.

C.A Musca, J. Antoszewski, K.J. Winchester, A.J. Keating, T. Nguyen, K.K.M.B.D. Silva, J.M. Dell, L. Faraone, P.Mitra, J. D. Beck, M.R. Skokan, J. E. Robinson, "*Monolithic Integration of an Infrared Photon Detector With a MEMS Based Tunable Filter*", IEEE Elec. Dev. Letts., vol. 26, No. 12, Dec. 2005, pp. 888-890.

Antoszewski, Jaroslaw; Keating, Adrian; Winchester, Kevin; Nguyen, Thuyen; Silva, Dilusha; Musca, Charles; Dell, John; Samardzic, Olivia; and Faraone, Lorenzo. Tunable Fabry-Perot Filters Operating in the 3 to 5 UM Range for Infrared Microspectrometer Applications, Proc. SPIE—vol. 6186, MEMS, MOEMS, and Micromaching II, 2006, 618608.

Keating, A.J.; Silva, K.K.M.B.D.; Dell, John; Musca, C.A.; and Faraone, L. "Optical Characterization of Fabry-Perot MEMS Filters Integrated on Tunable Short-Wave IR Detectors." IEEE Photonics Technology Letters, vol. 18, Issue 9, May 1, 2006, pp. 1079-1-81.

Rivas, Anette; Kerekes, John; and Raisanen, Alan, "Tunable Singel Pixel MEMS Fabry-Perot Interferometer." Adaptive Optics: Methods, Analysis and Applications Toronto, Canada, Jul. 10, 2011, Joint FTS/HISE/AO/COSI Poster Session (JWA), JWA15.Pdf.

Cleary, Justin W.; Fredricksen, Chris J.; Muravjov, Andrei V.; Enz, Jasen; Dolguikh, Maxim V.; Du Bosq, Todd W.; Peale, Robert E.; Folks, William R.; Pandey, Sidhartha; Boreman, Glenn; and Edwards, Oliver;"Scanning Fabry-Perot Filter for Terahertz Spectroscopy Based on Silicon Dielectric Mirrors", SPIE vol. 6472, 2007.

Cleary, Justin W.; Peale, Robert E.; Todi, Ravi; Sundaram, Kalpathy; and Edwards, Oliver;Finesse of Silicon-Based Theraherz Fabry-Perot Spectrometer, SPIE, 6549-26, vol. 5, Mar. 11, 2007.

Du Bosq, Todd W.; Muravjos, Andrey V.; Peale, Robert E.; and Fredericksen, Christopher J.; "Multilayer Silicon Cavity Mirrors for the Far-Infrared p-Ge Laser"; Applied Optics, vol. 44. No. 33, Nov. 20, 2005.

\* cited by examiner

COMPACT THZ FOCAL PLANE IMAGING ARRAY WITH INTEGRATED CONTEXT IMAGING SENSORS AND ANTENNAE MATRIX

FIELD OF THE INVENTION

The present invention relates, in general, to imaging technology. More specifically, the present invention relates to a compact THz detector with multiple antennae and multiple electronics circuits per pixel cell arranged in a focal plane array.

BACKGROUND OF THE INVENTION

THz detection has many applications. These applications include concealed weapon detection, surveillance cameras, astronomy, non-destructive material testing, as well as ample biological and medical applications. The most common THz detectors currently available are single, or sparse element scanning systems, which typically use heterodyne detection with high speed Schottky diode mixers.

However, there are many shortcomings with current THz detectors. There is an ever present need for THz detectors with a higher quantum efficiency, a higher level of detector integration in low cost, non-bulky systems, and an improved signal-to-noise ratio (SNR).

SUMMARY OF THE INVENTION

To meet this and other needs, and in view of its purposes, the present invention provides a monolithic focal plane array (FPA) comprising: an array of multiple pixel unit cells disposed on a substrate. Each pixel unit cell includes: (a) a first array of THz antennae disposed on a top layer of the substrate, and (b) a second array of context imaging pixels disposed on the top layer of the substrate. The first and second arrays are interleaved on the top layer of the substrate.

Each THz antenna in the first array is shaped in a bow-tie configuration, and each context imaging pixel in the second array is shaped in a circular, or rectangular configuration. The bow-tie configuration includes two triangles extending away from a common apex and ending in two opposing bases. A column of the first array includes a vertical line passing through respective apexes of multiple THz antennae disposed in the column. A context imaging pixel of the second array is disposed along the vertical line between two THz antennae disposed in the column.

A semiconductor layer is disposed below the top layer of the substrate. The semiconductor layer includes first and second circuits for processing signals received from the first and second arrays, respectively. An interconnect layer is disposed between the top layer and the semiconductor layer for providing couplings between the first and second arrays and the first and second circuits, respectively. The first circuit includes a summing circuit for summing each signal from a THz antenna disposed in the first array, and the first circuit provides a pixel output representing a summation of signals from the THz antennae disposed in the first array of a single pixel unit cell.

A mixer is included for multiplying each signal from the THz antenna with a signal from a local oscillator and providing the multiplied signal from the mixer to the summing circuit. A waveguide is included for coupling each signal from the THz antenna with the mixer.

The second circuit includes an averaging circuit for averaging signals received from the context imaging pixels in the second array, and the second circuit provides a pixel output representing an average of the context imaging pixels disposed in the second array of a single pixel unit cell.

Another embodiment of the present invention is a monolithic focal plane array (FPA) comprising an array of multiple pixel unit cells disposed on a substrate. Each pixel unit cell includes: (a) a first array of rows and columns of THz antennae disposed on a top layer of the substrate, and (b) a second array of rows and columns of context imaging pixels disposed on the top layer of the substrate. The first array and the second array are interleaved on the top layer, and the first array is denser in pitch than the second array.

Each THz antenna in the first array is configured to detect a signal in a THz band, and each context imaging pixel in the second array is configured to detect a signal in a visible band or a short wave infrared (SWIR) band.

The THz antennae are each configured as a dipole, in which each dipole is disposed in a respective row and column of the first array. Each dipole is spaced by an area from each other dipole, the area defined as a dipole-free area, and each context imaging pixel in the second array is disposed in a dipole-free area. The total number of dipole free areas are greater than a number of context imaging pixels in the second array.

The rows and columns of the first array of one pixel unit cell includes THz antennae that are vertically polarized, and the rows and columns of the first array of an adjacent pixel unit cell includes THz antennae that are horizontally polarized.

The rows and columns of the first array of one pixel unit cell includes THz antennae that are circularly polarized.

The rows and columns of the first array of one pixel unit cell includes THz antennae that are polarized in one direction, defined at an angle of 0 degrees, and the rows and columns of the first array of an adjacent pixel unit cell includes THz antennae that are polarized in a different direction of 90 degrees from the one direction.

Yet another embodiment of the present invention is an imager including a compact focal plane array (FPA) having multiple pixel unit cells. Each pixel unit cell comprises: a first matrix of THz antennae disposed on one layer of a substrate for receiving THz signals, and a second matrix of context imaging pixels disposed on an adjacent layer of the substrate for receiving visible or short wave infrared (SWIR) signals. The first and second matrices are exposed to the THz signals and the SWIR signals impinging on the substrate.

The imager includes a first image processor for processing the FPA using row and column scanners for sequentially scanning a summed signal from each pixel unit cell in the FPA. The summed signal is a summation of signals from each THz antenna in the first matrix. Each summed signal includes a coherent summation of each signal detected by each THz antenna in the first matrix.

The imager includes a second image processor for processing the FPA using row and column scanners for sequentially scanning an averaged signal from each pixel unit cell in the FPA. The averaged signal is an average of signals from each context imaging pixel in the second matrix.

It is understood that the foregoing general description and the following detailed description are exemplary, but are not restrictive, of the invention.

BRIEF DESCRIPTION OF THE FIGURES

The invention may be understood from the following detailed description when read in connection with the accompanying figures.

DETAILED DESCRIPTION OF THE INVENTION

The present invention provides a monolithic integrated, high pixel density, THz focal plane array (FPA) sensor, in which each pixel unit cell contains multiple THz antennae and multiple electronics processing elements. The density of THz antennae in each pixel unit cell of the FPA improves the signal-to-noise-ratio (SNR) of the integrated THz FPA sensor. The present invention also integrates context imaging pixels, or sensors that are configured to capture visible band and/or short wave infrared (SWIR) band signals within each pixel unit cell. The context imaging pixels enhance visualization and interoperability for the user.

Figure 1:
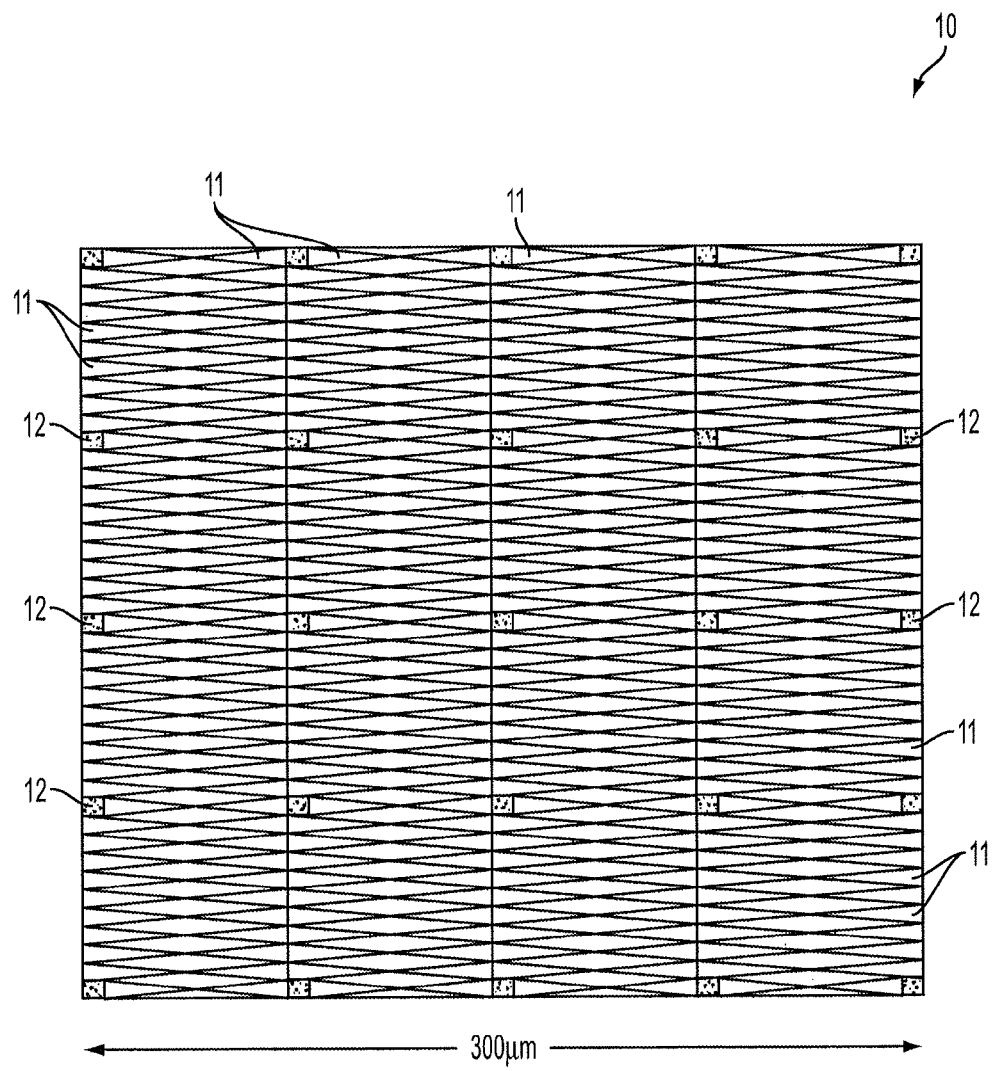
FIG. 1 is a planar view of a single pixel unit cell of a focal plane array (FPA), the pixel unit cell including multiple antennae and multiple context imaging sensors, in accordance with an embodiment of the present invention.

FIG. 1 is a planar view of a single pixel unit cell of a THz FPA sensor, the pixel unit cell generally designated as 10, in accordance with one embodiment of the present invention. The pixel unit cell 10 has length and width dimensions of about 300 um by 300 um. The top surface of pixel unit cell 10 includes a plurality of antennae 11 and several context imaging pixels 12, each arranged in an array formation. Each antenna 11 disposed on pixel unit cell 10 has a length dimension of about 75 um and a width dimension of less than 10 um. The number of antennae 11 on pixel unit cell 10, as shown in FIG. 1, may be up to 160 antennae (for example). As shown, antennae array 11 is configured as an array having 4 columns by 40 rows. Each antenna 11 is shaped like a bow-tie, as best shown in FIG. 2A, 2B, or 2C.

Context imaging pixels 12, which are shown as rectangular and shaded darker than the antenna array, are also disposed on pixel unit cell 10. As shown the context imaging pixels are arranged as an array of 5×5 pixels in each pixel unit cell 10. Context imaging pixels 12 may be configured to capture visible band signals and/or short wave infrared (SWIR) signals. The different relationships amongst the context imaging pixels and each antenna in the antennae array are best shown, as examples, in FIG. 2A, 2B, or 2C.

Figure 2A:
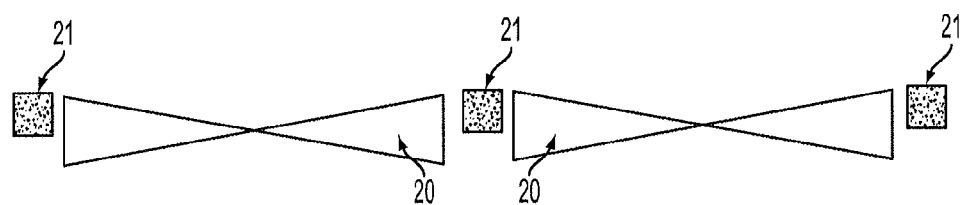
FIGS. 2A-2C illustrate different arrangements of context imaging sensors in relation to antenna arrays, as they are positioned in a single pixel unit cell, in accordance with various embodiments of the present invention.
Figure 2B:
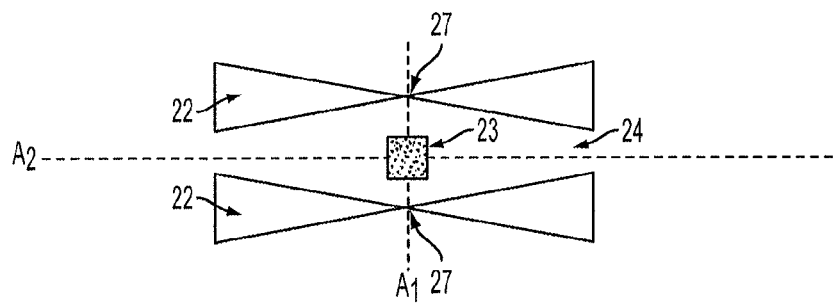
Figure 2C:
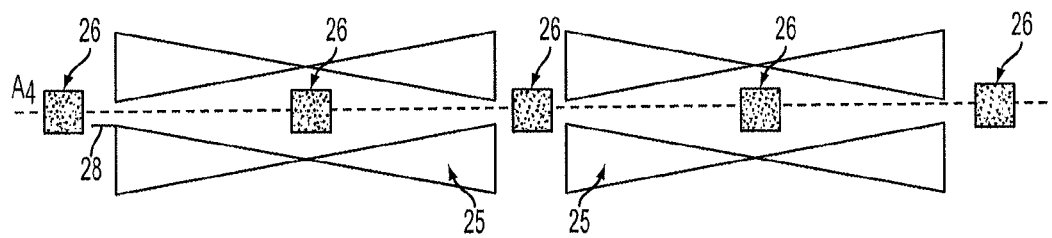

Referring next to FIGS. 2A-2C, there is shown multiple arrangements of antennae with context imaging pixels. The antennae shown (20, 22, 25) are of a bow-tie configuration. Other suitable antennae configurations will be understood by one of skill in the art from the description herein.

As shown in FIG. 2A, context imaging pixels 21 (three are shown) are positioned adjacent ends of each antenna 20 (two are shown). This arrangement is similar to the arrangement of context imaging pixels 12 on pixel unit cell 10 in FIG. 1. It will be appreciated that although each context imaging pixel 21 is shown as having a rectangular shape, it may be any other shape, for example, elliptical or circular.

FIG. 2B depicts a different arrangement of context imaging pixels in relation to a THz antennae array. As shown, context imaging pixel 23 (one shown) is positioned between two opposing bow-tie antennae 22 at the intersection of axes $A_1$ and $A_2$. Axis $A_1$ vertically bisects bow-tie antennae 22 at their center points 27. Axis $A_2$ horizontally bisects the spacing 24 between the two bow-tie antennae 22.

FIG. 2C shows yet another example of a relationship between multiple context imaging pixels and a THz antennae array (only four are shown). As shown, context imaging pixels 26 (five are shown) are positioned along horizontal axis $A_4$. Axis $A_4$ horizontally bisects spacing 28 between two rows of antennae 25.

It will be understood that the context imaging pixels (21, 23, or 26), which are depicted in FIGS. 2A-2C, respectively, may be interleaved on a single pixel unit cell (such as pixel unit cell 10 in FIG. 1). In addition, each THz imaging system includes many pixel unit cells. For example, a THz imaging system may include an array of 800×800 pixel unit cells, in which each pixel unit cell (such as unit cell 10) includes an interleaved configuration of multiple context imaging pixels and an antennae array. Assuming a THz imaging system comprised of an array of 800×800 pixel unit cells and assuming the interleaved arrangement shown in FIG. 1 of antennae array 11 and context imaging pixel array 12, then there would be 800×800×160 THz antennae and 800×800×25 context imaging pixels in each THz imaging system of the present invention.

The inventors discovered that interferences amongst the context imaging pixels (12, 21, 23, 26) and the antennae (11, 20, 22, 25) are minimal. Therefore, it is contemplated that many different interleaved arrangements of antennae with context imaging pixels on a single pixel unit cell are possible. The figures shown herein include only a few of the possible examples of the present invention.

Figure 3B:
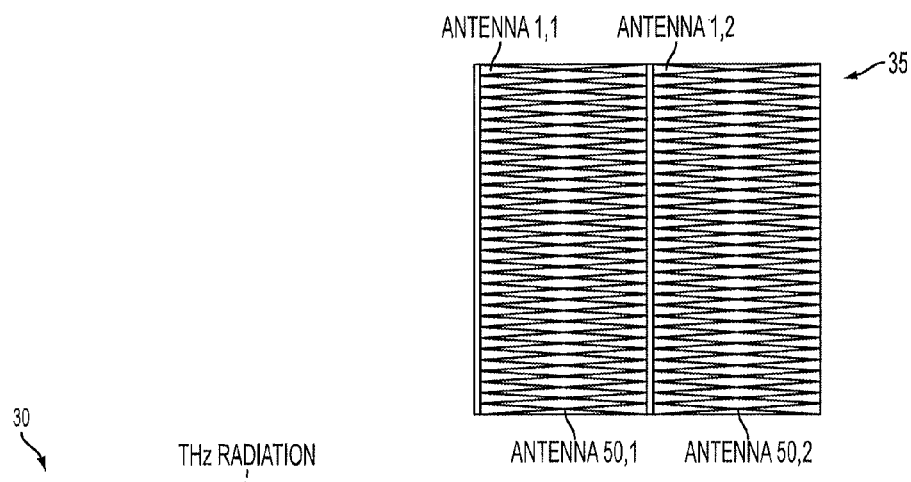
FIG. 3B is a planar view of the antenna array on the pixel unit cell shown in FIG. 3A, in accordance with an embodiment of the present invention.
Figure 3A:
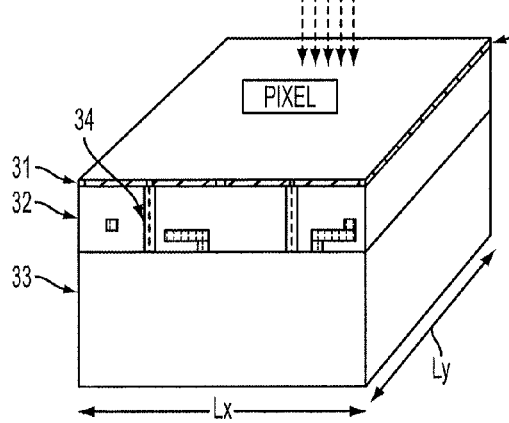
FIG. 3A is a perspective view of a single pixel unit cell, which includes an antenna array and an array of context imaging sensors, in accordance with an embodiment of the present invention.

Referring next to FIG. 3A, there is shown a perspective view of a single pixel unit cell, generally designated as 30, in accordance with an embodiment of the present invention. The pixel unit cell 30, as an example, may have nominal in-plane dimensions (Lx, Ly) of about 300 um×300 um. The pixel unit cell 30 includes several layers, in which only three layers are shown, such as a top planar layer 31, a semiconductor layer 33, and an interconnect layer 32. The interconnect layer is disposed between antenna layer 31 and semiconductor layer 33. The top planar layer 31 may include two separate deposition layers, a first deposition layer being the antennae array layer (an example shown in FIG. 3B, as antennae array 35) and a second deposition layer being the context imaging pixel array layer (an example shown in FIG. 3C, as context imaging pixel array 38).

The semiconductor layer 33 may include a CMOS or BiC-MOS substrate. In embodiments where semiconductor layer 33 includes a CMOS substrate, the THz FPA sensor system may be fabricated in a standard CMOS foundry process, utilizing low bandwidth resistive self-mixing field-effect transistors (FETs). In embodiments where semiconductor layer 33 includes a BiCMOS substrate, the THz FPA sensor system may be fabricated in a high speed BiCMOS SiGe foundry process (e.g., IBM 9-HP) enabling use of high bandwidth (e.g., greater than about 300 GHz) direct detection amplifiers that are capable of responding at full THz bandwidth.

The interconnect layer 32 may be an assembly of several layers disposed above semiconductor layer 33. Each interconnect layer 32 may include metallic vias and strips, which allow the antennae array and the context imaging pixel array to be coupled to high gain amplifiers (not shown). The interconnect layer 32, as shown, includes multiple waveguides 34, with each waveguide 34 coupling a respective antenna in the antennae array to other circuits, such as high gain amplifiers.

The top planar layer 31, as shown, includes a deposition layer of antennae array 35 and another deposition layer of context imaging pixels array 38. Referring to FIG. 3B, there is shown a planar view of antennae array 35 to be deposited on top of planar layer 31, in accordance with an embodiment of the present invention. Antennae array 35 includes a multiplicity of antennae, each of which may be tuned to a desired THz wavelength. Each antenna in antenna array 35 may be a dipole antenna and, for example, may be configured in a bow-tie shape having two triangular sides, as shown in FIG. 2A, 2B, or 2C. Each triangular side of the dipole antenna is a quarter wavelength in length. Each antenna in antenna array 35 is spaced from adjacent antennae to reduce interference. As shown, per single pixel cell unit 30, antenna array 35 is comprised of one hundred antennae, arranged in two columns by fifty rows, with vertical and horizontal spacing (as shown, for example, in FIG. 2A, 2B, or 2C) of about 6 um. Each antenna in antennae array 35 is labeled in a column by row designation, such as antenna 1,1, antenna 1,2, . . . , antenna 50,1 and antenna 50,2.

In an alternative embodiment, antenna array 35 includes one hundred and twenty antennae arranged in two columns by sixty rows, with spacing of about 5 um between each respective antenna. In yet another embodiment, antenna array 35 includes two hundred and forty antennae arranged in four columns by sixty rows, with spacing of about 5 um between each respective antenna. Each antenna in antennae array 35 is coupled to a device fabricated in semiconductor layer 33, by way of a waveguide 34, the latter disposed in interconnect layer 32.

Figure 3C:
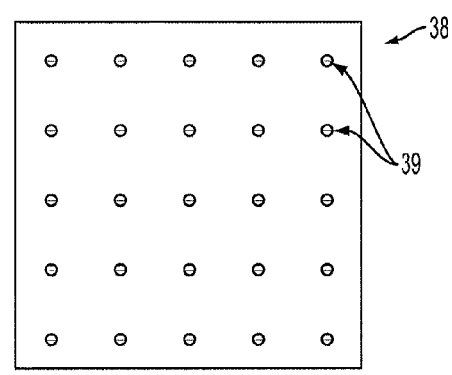
FIG. 3C is a planar view of the array of context imaging sensors on the pixel unit cell shown in FIG. 3A, in accordance with an embodiment of the present invention.

The second deposition layer is shown in FIG. 3C, as a planar view of an exemplary arrangement of an array 38 of context imaging pixels 39. The array 38 includes five columns by five rows of pixels, thereby obtaining 25 context imaging pixels that are interleaved with 100 antennae on top planar layer 31. Again, it will be understood that both arrays are interleaved on the top planar layer of each single pixel unit cell of the THz FPA imaging system of the present invention.

Each context imaging pixel 39, for example, is about 5 um×5 um. The size of each context imaging pixel 39 may vary with the size of pixel unit cell 30. Each context imaging pixel 39 may be spaced from adjacent context imaging pixels by a distance smaller than the length of the unit cell's pitch in the THz FPA imaging system. Each context imaging pixel 39 may be configured to capture signals in the visible band and/or the SWIR band.

Figure 4:
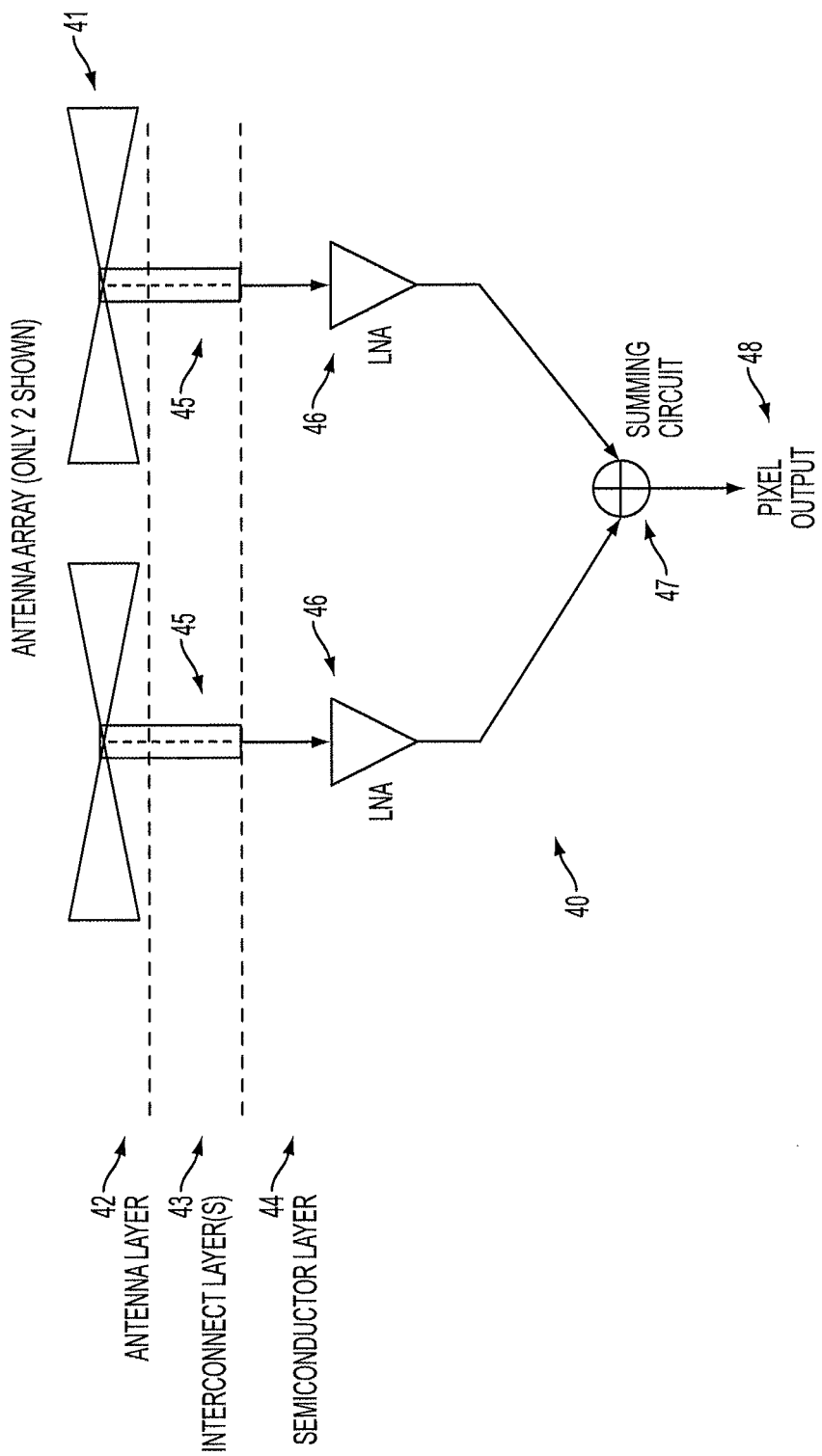
FIG. 4 is a circuit block diagram of a portion of a pixel unit cell including an antenna array configured with a summation circuit, in accordance with an embodiment of the present invention.

Referring next to FIG. 4, there is shown a circuit block diagram of a portion of a pixel unit cell for summing the signals sensed by multiple antennae in the antennae array, designated generally as 41. The multiple antennae in array 41 are disposed in antenna layer 42 of the pixel unit cell. Each antenna in antennae array 41 is configured in a bow-tie shape. Other suitable antenna shaped configurations will be understood by one skilled in the art.

Each antenna in array 41 is coupled to a low noise amplifier (LNA) 46, which is disposed in semiconductor layer 44. The coupling is accomplished by a waveguide 45, which is disposed in interconnect layer 43. Each antenna in the array detects a THz signal which is sent to a respective LNA 46 via a respective waveguide 45. Each LNA 46 amplifies the detected signal to a voltage level which is summed with other amplified detected signals from other antennae in the array. The summations are incoherently performed by summing circuit 47, thereby providing a pixel output 48 from the respective unit pixel cell in the THz FPA sensor system. It will be understood that each antenna in array 41 may have a separate LNA 46, such that the number of LNAs in a pixel unit cell is equal to the number of antennae in the array. In the example of FIG. 4, each antenna disposed on layer 42 in the single pixel unit cell is summed by summing circuit 47 to produce one pixel output 48. Accordingly, if there are 800× 800 pixel unit cells, for example, in a THz FPA sensor system, then there would be 800×800 pixel output signals 48.

FIG. 4 shows the summing circuit located in semiconductor layer 44. In an alternative embodiment, summing circuit 47 may be located externally of each pixel unit cell.

Figure 5:
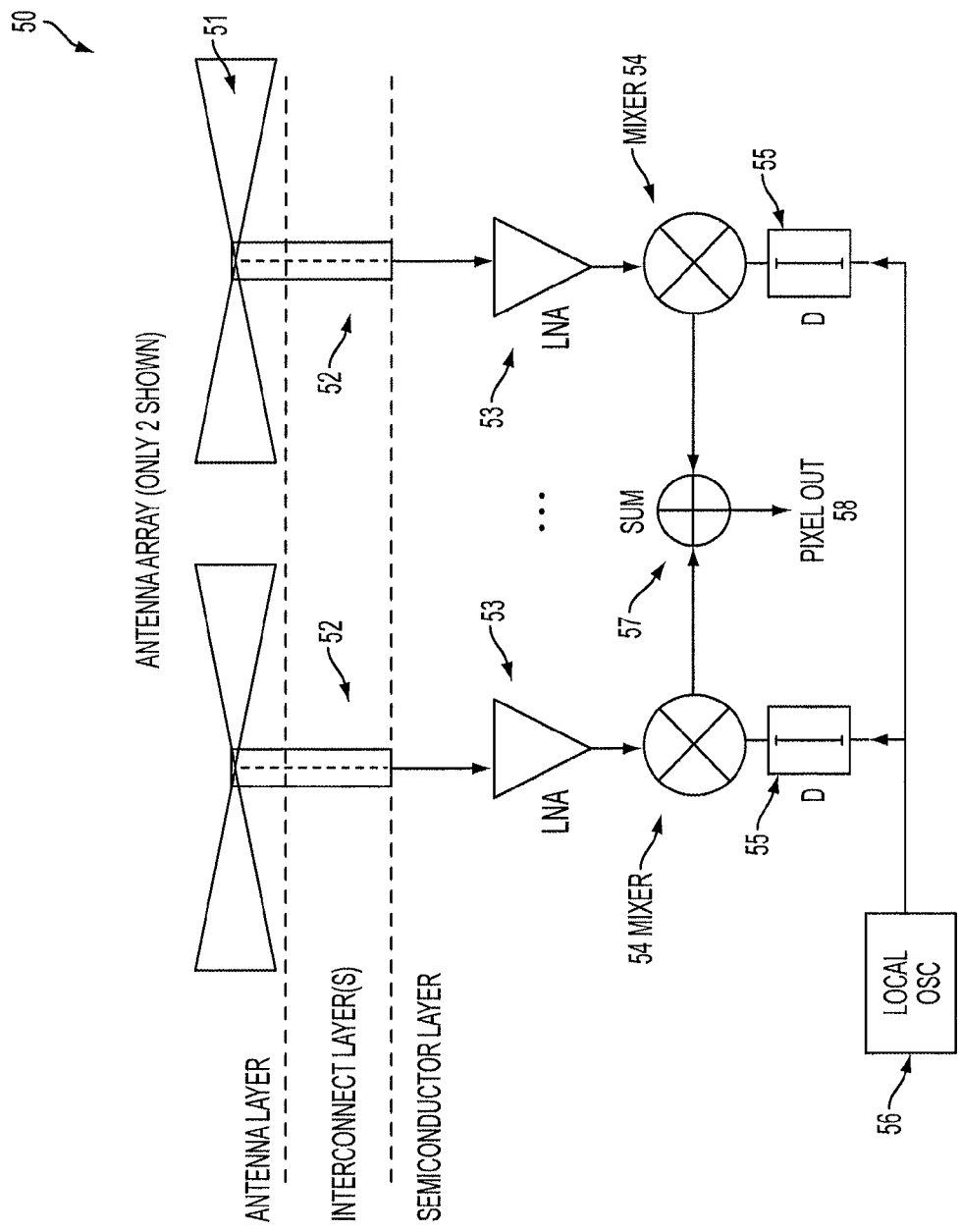
FIG. 5 is a circuit block diagram of a portion of a pixel unit cell including an antenna array configured for coherent summation, in accordance with an embodiment of the present invention.

Reference is now made to FIG. 5, which shows another embodiment in the summation of signals detected by an antennae array. Different from the summation shown in FIG. 4, the summation shown in FIG. 5 is performed coherently, as depicted by a portion of a pixel unit cell. As shown, each antenna (two are shown) in array 51 are configured in a bow-tie shape. Each antenna in the array is coupled to a respective LNA 53, which is disposed in the semiconductor layer. Each antenna in array 51 detects a THz signal which is sent to a respective LNA 53 via a respective waveguide 52. Each LNA 53 amplifies the signal and sends it to a respective mixer 54. Each mixer 54 multiplies the detected signal with a known signal from a local oscillator 56. The signal arriving from the local oscillator is delayed as necessary by a respective delay line 55. This enables coherent summation of all the multiplied signals by way of summation circuit 57.

The summed signal is provided as a pixel output signal 58 and corresponds to a coherent summation of all the detected signals from antenna array 51 disposed in a single pixel unit cell. As previously noted, there are numerous pixel unit cells in each THz FPA sensor system. Accordingly, there are multiple pixel output signals 58 that correspond to the multiple pixel unit cells in the THz FPA sensor system.

As known in the art, mixer 54 may be a heterodyne mixer. In an embodiment where mixer 54 is a heterodyne mixer, the mixer is configured to down convert the amplified signal. Although not depicted, each antenna in array 51 disposed on the antenna layer may have a discrete LNA 53 and a mixer 54. Thus, the number of LNAs and mixers in a pixel unit cell equals the number of antenna in array 51.

As shown in FIG. 5, local oscillator 56 is disposed externally of the pixel unit cell. The local oscillator, which may be shared by many, or all the pixel unit cells in the THz FPA sensor system, may be programmable or fixed.

Figure 6:
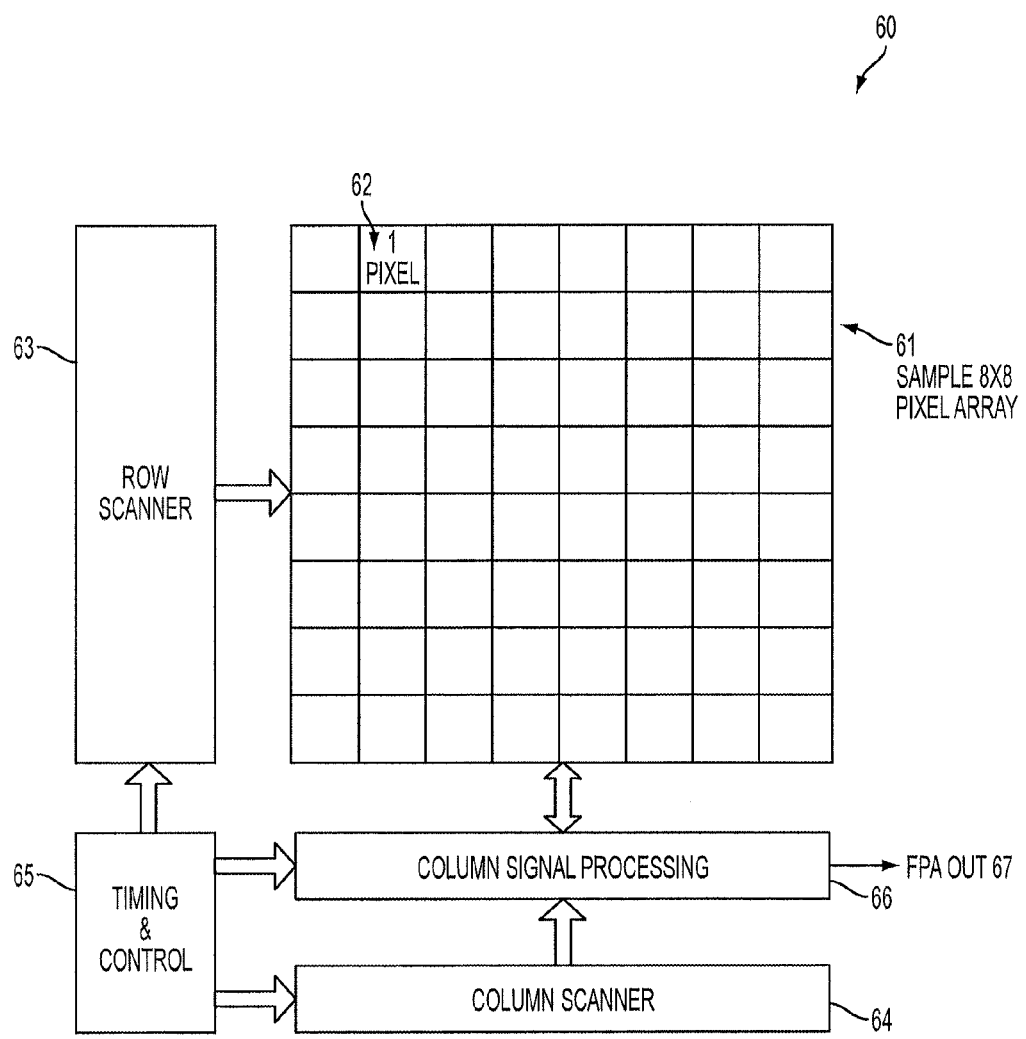
FIG. 6 is a diagram of an image processor configured for use with embodiments of the present invention.

FIG. 6 illustrates a signal processor, generally designated as 60, as an example of an architecture configured for processing the output signals from each pixel unit cell in the THz FPA sensor system. In the example, an 8×8 unit cell array 61 is shown. Each unit cell is designated as 62. As known in the art, signal processor 60 is configured to sequentially read-out the entire array of pixels in a system having pixels in an FPA.

Thus, processor 60 provides as an output the columns in every sequential row of the FPA, the output generally shown as FPA output 67.

Thus, signal processor 60 may be used to read-out, in sequence, each pixel output 48 (FIG. 4) or each pixel output 58 (FIG. 5) disposed in the THz FPA sensor system, thereby providing a non-coherent FPA output or a coherent FPA output, respectively.

Completing the description of signal processor 60, a row scanner 63 and a column scanner 64 are provided to sequentially scan each signal outputted from each summing circuit in each pixel unit cell 62. Timing and control logic circuit 65 controls row scanner 63 and column scanner 64. The sequential output signals provided from the unit pixels in the THz FPA sensor system are processed by a column signal processor 66. The column signal processor outputs the processed signals as the FPA image read-out.

It will be understood that the aforementioned description pertains to the FPA image read-out obtained by processing the signals from each summation circuit (47 in FIG. 4, or 57 in FIG. 5) in the THz FPA sensor system. In a similar manner, the array of image context pixels that are disposed in each top planar layer of a respective pixel unit cell may also be processed by a separate signal processor system 60.

With respect to the processing of the image context pixels, however, there are much fewer context pixels in the THz FPA sensor system than there are THz antennae. Therefore, the present invention may dispense with having to sum (more precisely, average) each image context pixel per unit cell. Instead, it is contemplated that the present invention may sequentially read each context pixel in the THz FPA sensor system, without needing to average the outputs of each context pixel in each unit pixel cell.

Alternatively, the process described above for the summation of each antenna in the array may also be used by averaging the output from each context pixel disposed in a respective unit cell. Then, the signal processor shown in FIG. 6 may be utilized to sequentially scan each averaged output from a respective unit pixel 62 in the array 61 of the THz FPA sensor system.

Figure 7B:
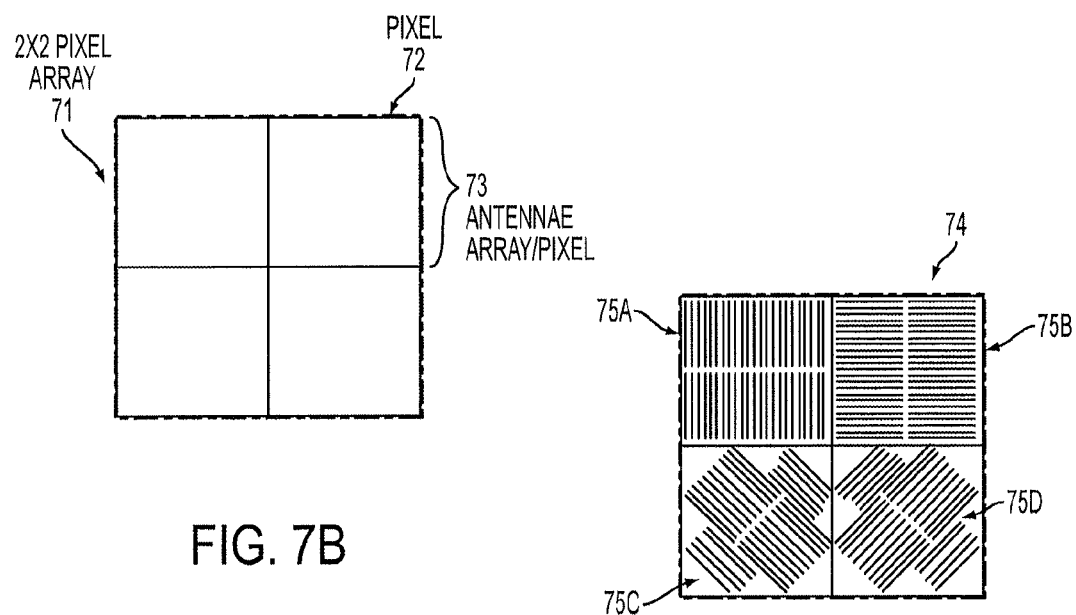
FIGS. 7A-7D are planar views of different antenna array orientations in an 8×8 pixel array.
Figure 7C:
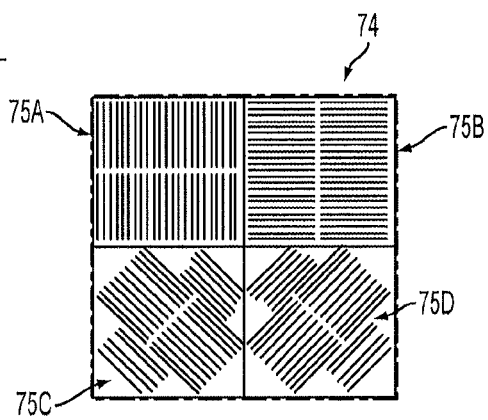
Figure 7A:
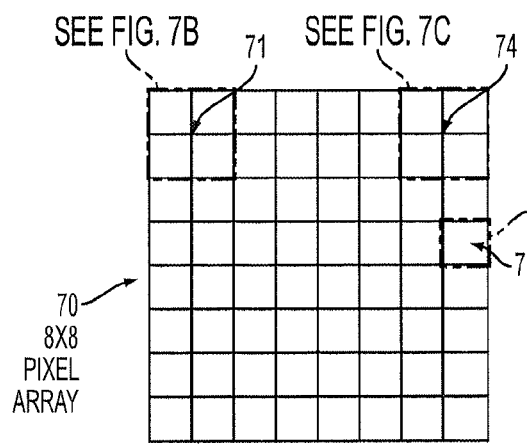

Referring now to FIGS. 7A-7D, there are shown planar views of different antennae array orientations in a unit pixel cell, in accordance with aspects of the present invention. Each of the antennae array orientations may be used to capture THz waves using various polarizations. As an example, FIG. 7A shows a THz FPA sensor system having an 8×8 pixel array, generally designated as 70. A magnified planar view of a portion of the THz FPA sensor system is shown in FIG. 76, as a 2×2 pixel array, designated as 71. Each pixel unit cell in the 2×2 array is designated as 72.

As an example, antennae array 73 includes two rows of THz antennae. The antennae array 73 includes antennae that are oriented in the same vertical direction. This allows the capture of THz signals having a vertical polarization of THz waves per unit pixel. Since all four unit pixels in the 2×2 array 71 have antennae that are vertically oriented, all four unit pixels would each sum (either coherently or incoherently) all the vertically polarized THz signals detected by a respective antennae array 73.

FIG. 7C provides another example of a magnified planar view of a 2×2 pixel array, designated as 74, which shows each pixel unit cell (75A, 75B, 75C, 75D) having antennae arrays oriented in different directions. Pixel unit cells 75A and 75B include antennae arrays that are orthogonal to each other; and pixel unit cells 75C and 75D include antennae arrays that are also orthogonal to each other. This configuration of pixel array 74 allows for each pixel unit cell to capture THz signals that are polarized, for example, at a relative angle of 0 degrees, 90 degrees, 180 degrees and 270 degrees.

Figure 7D:
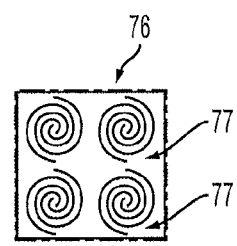

Referring next to FIG. 7D, there is shown a magnified planar view of yet another example of a pixel unit cell 76. This pixel unit cell includes an array of four omni-directional spiral antennae 77. The orientation of antennae 77 allows pixel unit cell 76 to capture signals from all polarizations of THz waves. It will be understood, however, that any combination of antennae orientations is contemplated by the present invention.

Figure 8:
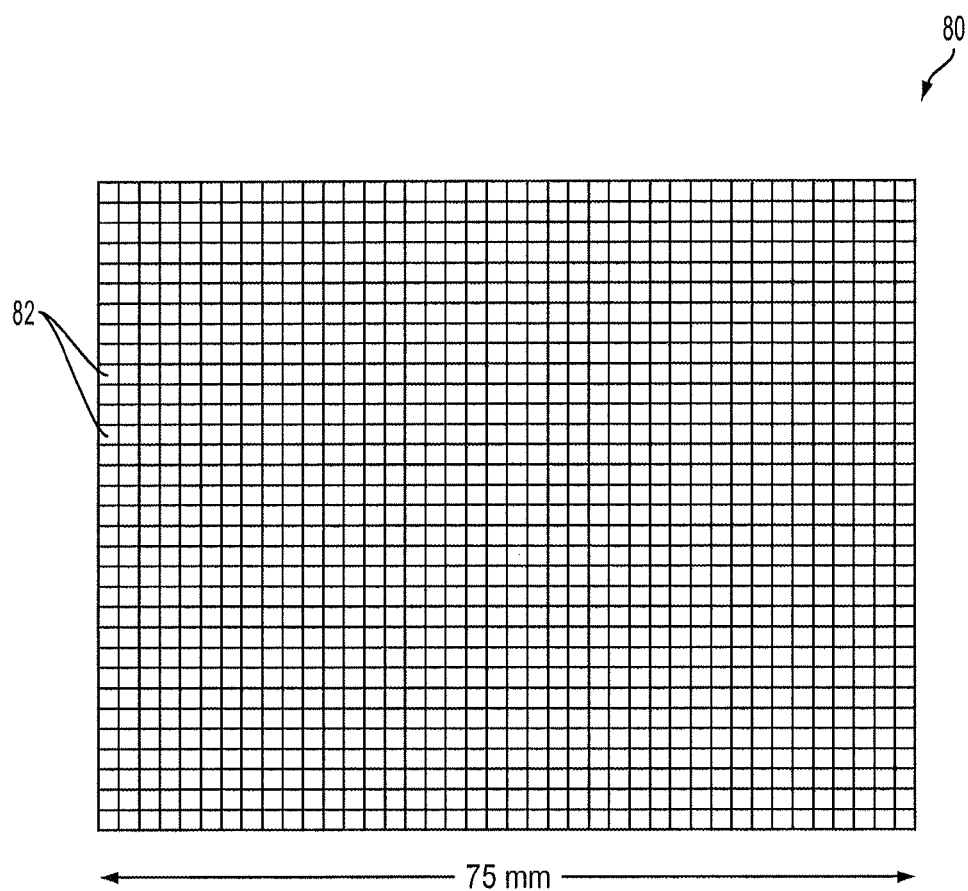
FIG. 8 is a planar view of a THz focal plane array sensor, in accordance with an embodiment of the present invention.

FIG. 8 is a planar view of a THz FPA sensor system, generally designated as 80. The THz FPA sensor system 80 has width and length dimensions of about 75 mm×75 mm and includes a 256×256 array of pixel unit cells, in which each pixel unit cell is designated as 82. Each pixel unit cell 82 is fabricated in accordance with aspects of the present invention. For example, each pixel unit cell 82 may include the antennae array and the context imaging pixels shown in FIG. 1. Moreover, the THz FPA sensor system 80 may include the image processor described with respect to FIG. 6.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A monolithic focal plane array (FPA) comprising:
an array of multiple pixel unit cells disposed on a substrate, in which each pixel unit cell includes:
a first array of THz antennae disposed on a top layer of the substrate, and
a second array of context imaging pixels disposed on the top layer of the substrate,
wherein the first and second arrays are interleaved on the top layer of the substrate, and further including:
a semiconductor layer disposed below the top layer of the substrate,
the semiconductor layer including first and second circuits for processing signals received from the first and second arrays, respectively, and
an interconnect layer disposed between the top layer and the semiconductor layer for providing couplings between the first and second arrays and the first and second circuits, respectively, wherein
the first circuit includes a summing circuit for summing each signal from a THz antenna disposed in the first array, and
the first circuit provides a pixel output representing a summation of signals from the THz antennae disposed in the first array of a single pixel unit cell.

2. The FPA of claim 1 wherein
each THz antenna in the first array is shaped in a bow-tie configuration, and
each context imaging pixel in the second array is shaped in a circular, or rectangular configuration.

3. The FPA of claim 2 wherein
the bow-tie configuration includes two triangles extending away from a common apex and ending in two opposing bases,
a column of the first array includes a vertical line passing through respective apexes of multiple THz antennae disposed in the column, and
a context imaging pixel of the second array is disposed along the vertical line between two THz antennae disposed in the column.

4. The FPA of claim 2 wherein
the bow-tie configuration includes two triangles extending away from a common apex and ending in two opposing bases,
a row of the first array includes two columns of multiple THz antennae, and
a context imaging pixel of the second array is disposed between opposing bases of the two columns.

5. The FPA of claim 4 wherein
each of the two columns of the first array includes a vertical line passing through respective apexes of the multiple THz antennae disposed in the two columns, and
another context imaging pixel of the second array is disposed along the vertical line between two THz antennae disposed in at least one of the two columns.

6. The FPA of claim 1 further including:
a mixer for multiplying each signal from the THz antenna with a signal from a local oscillator and providing the multiplied signal from the mixer to the summing circuit.

7. The FPA of claim 6 further including:
a waveguide for coupling each signal from the THz antenna with the mixer.

8. The FPA of claim 1 wherein
the second circuit includes an averaging circuit for averaging signals received from the context imaging pixels in the second array, and
the second circuit provides a pixel output representing an average of the context imaging pixels disposed in the second array of a single pixel unit cell.

9. A monolithic focal plane array (FPA) comprising:
an array of multiple pixel unit cells disposed on a substrate, in which each pixel unit cell includes:
a first array of rows and columns of THz antennae disposed on a top layer of the substrate, and
a second array of rows and columns of context imaging pixels disposed on the top layer of the substrate,
wherein the first array and the second array are interleaved on the top layer, and
the first array is denser in pitch than the second array, and
each THz antenna is configured as a dipole, in which each dipole is disposed in a respective row and column of the first array,
each dipole is spaced by an area from each other dipole, the area defined as a dipole-free area, and
each context imaging pixel in the second array is disposed in a dipole-free area, and
a total number of dipole free areas are greater than a number of context imaging pixels in the second array.

10. The FPA of claim 9 wherein
each THz antenna in the first array is configured to detect a signal in a THz band, and
each context imaging pixel in the second array is configured to detect a signal in a visible band or a short wave infrared (SWIR) band.

11. The FPA of claim 9 wherein
the rows and columns of the first array of one pixel unit cell includes THz antennae that are vertically polarized, and
the rows and columns of the first array of an adjacent pixel unit cell includes THz antennae that are horizontally polarized.

12. The FPA of claim 9 wherein
the rows and columns of the first array of one pixel unit cell includes THz antennae that are circularly polarized.

13. The FPA of claim 9 wherein
the rows and columns of the first array of one pixel unit cell includes THz antennae that are polarized in one direction, defined at an angle of 0 degrees, and
the rows and columns of the first array of an adjacent pixel unit cell includes THz antennae that are polarized in a different direction of 90 degrees from the one direction.

14. An imager including a compact focal plane array (FPA) having multiple pixel unit cells, wherein each pixel unit cell comprises:
a first matrix of THz antennae disposed on one layer of a substrate for receiving THz signals, and
a second matrix of context imaging pixels disposed on an adjacent layer of the substrate for receiving visible or short wave infrared (SWIR) signals,
wherein the first and second matrices are exposed to the THz signals and the SWIR signals impinging on the substrate,
each THz antenna is configured as a dipole, in which each dipole is disposed in a respective row and column of the first matrix,
each dipole is spaced by an area from each other dipole, the area defined as a dipole-free area, and
each context imaging pixel in the second matrix is disposed in a dipole-free area, and
a total number of dipole free areas are greater than a number of context imaging pixels in the second matrix, and
the total number of THz antennae is greater than the number of context imaging pixels.

15. The imager of claim 14 including:
a first image processor for processing the FPA using row and column scanners for sequentially scanning a summed signal from each pixel unit cell in the FPA,
wherein the summed signal is a summation of signals from each THz antenna in the first matrix.

16. The imager of claim 15 wherein
each summed signal includes a coherent summation of each signal detected by each THz antenna in the first matrix.

17. The imager of claim 14 including:
a second image processor for processing the FPA using row and column scanners for sequentially scanning an averaged signal from each pixel unit cell in the FPA,
wherein the averaged signal is an average of signals from each context imaging pixel in the second matrix.

* * * * *